United States Patent [19]
Walmsley et al.

[11] Patent Number: 5,674,255
[45] Date of Patent: Oct. 7, 1997

[54] DUAL CHAMBER PACER HAVING AUTOMATIC PVARP

[75] Inventors: Frank R. Walmsley, North Oaks; Arthur L. Olive, Stacy; Jan Pieter Heemels, Minneapolis, all of Minn.

[73] Assignee: Cardiac Pacemakers, Inc., St. Paul, Minn.

[21] Appl. No.: 572,858

[22] Filed: Dec. 14, 1995

[51] Int. Cl.⁶ ................................................. A61N 1/368
[52] U.S. Cl. ........................................................... 607/14
[58] Field of Search ........................... 607/14, 17, 25, 607/9

[56] References Cited

U.S. PATENT DOCUMENTS

| | | |
|---|---|---|
| 4,686,989 | 8/1987 | Smyth et al. ............................ 607/14 |
| 4,890,617 | 1/1990 | Markowitz . |
| 4,951,667 | 8/1990 | Markowitz et al. . |
| 5,074,308 | 12/1991 | Sholder et al. ........................... 607/27 |
| 5,103,820 | 4/1992 | Markowitz . |
| 5,129,393 | 7/1992 | Brumwell . |
| 5,423,868 | 6/1995 | Nappholz et al. ......................... 607/14 |
| 5,496,350 | 3/1996 | Lu .............................................. 607/14 |
| 5,507,783 | 4/1996 | Buchanan .................................. 607/14 |

*Primary Examiner*—William E. Kamm
*Assistant Examiner*—Kennedy J. Schaetzle
*Attorney, Agent, or Firm*—Haugen and Nikolai, P.A.

[57] ABSTRACT

A dual chamber pacemaker incorporating an adaptive PVARP for breaking pacemaker mediated tachycardia episodes and adjusting the PVARP interval in a way that reduces future incidences of PMT without extending PVARP beyond what is required.

11 Claims, 2 Drawing Sheets

DUAL CHAMBER PACER HAVING AUTOMATIC PVARP

BACKGROUND OF THE INVENTION

I. Field of the Invention

This invention relates generally to the field of cardiac rhythm management devices, and more particularly to a dual chamber cardiac pacemaker or defibrillator incorporating a means for preventing pacemaker mediated tachycardia (PMT) also referred to as endless loop tachycardia (ELT).

II. Discussion of the Prior Art

In dual chamber pacemakers, circuitry is provided for both sensing atrial and ventricular depolarization events and for pacing one or both of atrial and ventricular tissue. When a subject has normal sinus node activity, but an interrupted conduction system, the pacemaker is able to sense an atrial depolarization (P-wave) and then stimulate the ventricle, following an established AV delay interval, thus effectively mimicking the heart's PR interval. A problem is created when a ventricular stimulating pulse causes a retrograde conducted P-wave to occur that is sensed by the atrial sensing circuitry if such retrograde conducted P-wave is permitted to initiate another ventricular stimulation event. To prevent this from occurring, dual chamber pacemakers commonly provide for a post ventricular atrial refractory period (PVARP). If an atrial event occurs during PVARP due to retrograde conduction, an AV interval is not initiated and no ventricular stimulating pulse is generated as a result of that atrial event.

In many pacemaker treated patients, however, the disease process is such that, typically, the retrograde conduction time varies depending upon physiologic feedback mechanisms. Hence, a fixed, programmable PVARP may become too short over time and may no longer serve to inhibit PMT. If, on the other hand, the programmed PVARP value is set to too large a value, thus shortening the sensing window, as the pacing rate reaches the maximum atrial tracking rate (MTR) established for the pacemaker, periodically P-waves will fall inside the PVARP interval and are ignored. This phenomenon is referred to as electronic Wenckebaching and results in a precipitous drop in ventricular rate, down to where every other P-wave is ignored (2:1 block). This sudden, radical drop in the ventricular pacing rate is a condition to be avoided for physiologic atrial tachycardia. If, on the other hand, PVARP is as small as possible, without having incidences of PMTs, the rate drop due to electronic Wenckebaching is not as precipitous and is less discomforting to the patient.

From the above, it can be deduced that it would be advantageous to incorporate in a DDD pacemaker an automatic or adaptive PVARP that will automatically extend the PVARP after an episode of PMT is detected while, at the same time, avoiding sudden shifts in the ventricular pacing rate as the maximum atrial tracking rate for the pacemaker is reached.

SUMMARY OF THE INVENTION

The above-described advantageous features are achieved in a DDD pacemaker that comprises sensing circuitry for detecting both atrial and ventricular depolarization events along with means for selectively stimulating one or both of an atrial chamber and a ventricular chamber. A first timing means is coupled to the atrial depolarization event sensing means for establishing an AV interval between the occurrence of an atrial depolarization event and the time at which the ventricular chamber stimulating means stimulates the ventricular chamber. A second timing means is also included and is coupled to the means for sensing ventricular depolarization events for establishing a PVARP time interval during which sensed atrial events are ignored and do not precipitate a ventricular stimulating pulse.

The pacemaker in accordance with this invention further includes a means for detecting the occurrence of pacemaker mediated tachycardia and a means responsive to the detecting means for breaking the PMT. This may comprise a means coupled to the second timing means for increasing the PVARP interval to a predetermined value that insures that retrograde P-waves are not tracked for at least one beat, and thereafter adding a first predetermined time increment value to the previously existing PVARP time interval. Other approaches for breaking the PMT may also be employed.

For example, and without limitation, the means for detecting the occurrence of pacemaker mediated tachycardia may comprise circuitry for sensing when the ventricular stimulating means is stimulating ventricular tissue at the maximum atrial tracking rate (MTR) over a predetermined number of beats. When such an event is detected, the PVARP interval may be extended for one beat to, say, 400 milliseconds, a value that should result in breaking of the PMT episode. Following that single beat extension, the original PVARP may be extended by a time increment of, for example, 20 milliseconds and this cycle would be repeated each time PMT episodes are detected with the original PVARP being extended by additional 20 ms increments. If no PMT episode is detected within a preprogrammed time interval, say, one or two months or even a year, the previously incremented PVARP may be decremented by, for example, ten milliseconds to thereby approach a minimum value of PVARP that will not result in episodes of PMT.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
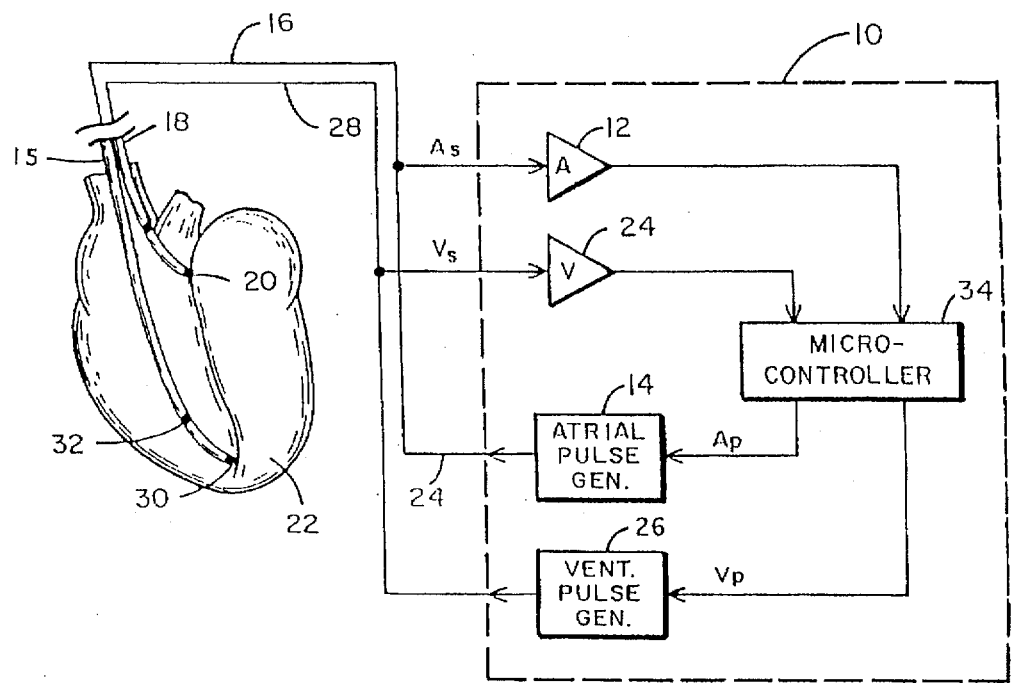
FIG. 1 is a general block diagram of a dual chamber pacemaker coupled to a heart by a pacemaker lead.

Referring to FIG. 1, there is shown enclosed by the broken line box 10 the operative components of a typical implantable dual chamber bradycardia pacemaker. The pacemaker 10 is seen to include an atrial sense amplifier 12 and atrial pulse generator 14 that are connected by wires 16 in a pacing lead 18 to a sensing and pacing electrode 20 disposed in the right atrium of a heart 22. The pacemaker 10 also includes a ventricular sense amplifier 24 and ventricular pulse generator 26 that are connected by a conductor 28 in the lead 18 to a sensing and pacing electrode 30 located in the right ventricle of the heart 22.

The above-description is for a unipolar lead system. Either or both leads can also be bipolar leads with a second electrode 32 as shown on the ventricular lead 15.

The outputs from the atrial sense amplifier 12 and the ventricular sense amplifier 24 are applied as inputs to a microprocessor-based microcontroller 34 which functions to control the time of application of atrial stimulating pulses ($A_p$) and ventricular stimulating pulses ($V_p$) to the heart in a coordinated fashion determined by the software executed by the microprocessor portion of the microcontroller 34.

Figure 2:
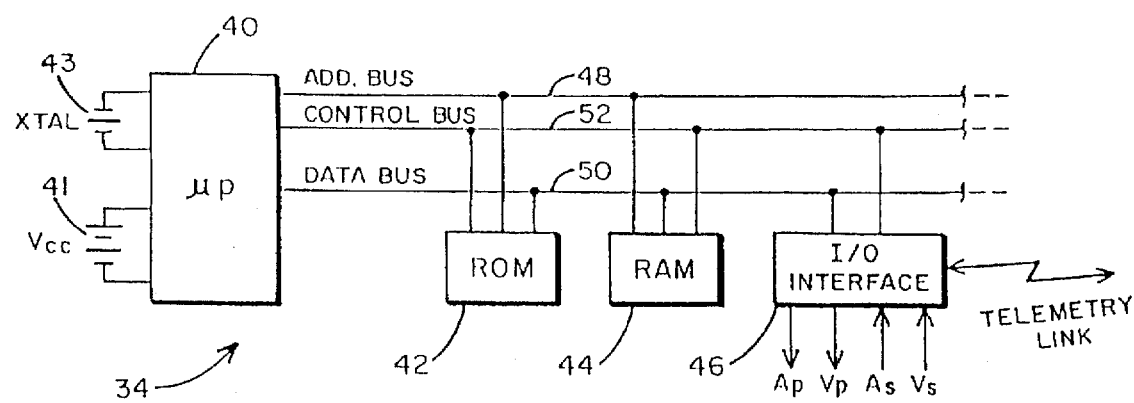
FIG. 2 is a block diagram of the microcontroller of the pacemaker of FIG. 1.

The microcontroller 34 is more particularly depicted in the block diagram of FIG. 2. It is seen to include a programmable microprocessor 40 formed as an integrated circuit that can be encapsulated along with a battery supply 41 within a hermetically sealed can as is well known in the art. The microprocessor 40 includes a clock oscillator whose frequency is controlled by a crystal 43 as well as the usual compliment of program counter, instruction decode logic, register stacks and an ALU, all of these components being conventionally found in present day prior art microprocessors. A variety of such microprocessors may be used in the implementation of the present invention.

As indicated in FIG. 2, the microprocessor 40 has associated with it a semiconductor ROM memory 42, a read/write or random access memory (RAM) 44, and an input/output interface 46 which are coupled to the microprocessor via an address bus 48, a data bus 50 and a control bus 52. The ROM memory 42 will typically contain a program of instructions while the RAM memory 44 will store programmable operands which may be telemetered into the implanted pacemaker 10 from an external programmer/monitor module (not shown) again, as is conventional in the art. In particular, the $A_s$ and $V_s$ inputs from the electrodes on the sensing/pacing leads 15 and 18 are applied to the microprocessor 40 via the I/O interface 46 and that interface is also used to couple the control signals $A_p$ and $V_p$ to the atrial pulse generator 14 and the ventricular pulse generator 26 at appropriate times as dictated by the program executed by the microprocessor 40.

Before describing the adaptive PVARP feature of the present invention, it is deemed helpful to have certain terminology defined:

Maximum Tracking Rate (MTR) is the maximum rate at which the paced ventricular rate will track sensed atrial events. It is applicable to the atrial synchronous pacing modes, DDD, DDDR, VVDR and VDD and is a programmable quantity typically residing in the range of from about 50 to 185 pulses per minute.

AV delay (AV) is the programmable time period from the occurrence of an atrial event, either sensed or paced, to a paced ventricular event. It is a programmable quantity typically ranging between 0 and 300 milliseconds and is active in DDD, DDI, DVI, DOO, VDD and the similar rate responsive modes.

Dynamic AV delay interval means that the AV delay interval changes as a function of the pacing rate.

Post Ventricular Atrial Refractory Period (PVARP) is defined as the time period after a ventricular event, either paced or sensed, during which activity in the atrium does not inhibit an atrial stimulation pulse nor trigger a ventricular stimulating pulse. It is designed to avoid atrial sensing of retrograde activity initiated in the ventricle.

Pacemaker Mediated Tachycardia (PMT). In DDD(R) and VDD(R) pacing modes, the pacemaker may detect retrograde conduction in the atrium, causing triggered ventricular pacing rates as high as the MTR. This is referred to in the literature as pacemaker-mediated tachycardia or endless loop tachycardia.

Total Atrial Refractory Period (TARP) is defined as the sum of the AV delay and PVARP.

Figure 3:
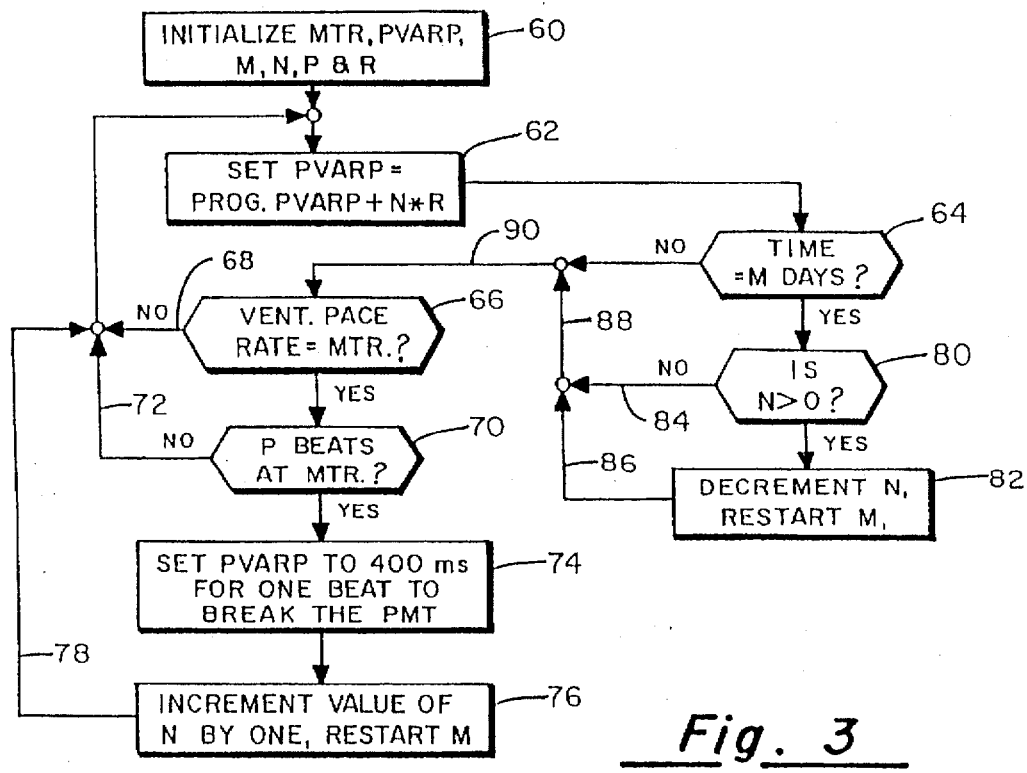
FIG. 3 is a software flow diagram of the portion of the program executed by the microcontroller for implementing adaptive PVARP.

Referring to FIG. 3, there is shown a software flow diagram of the algorithm implemented in the software executed by the microprocessor 40 of FIG. 2 in implementing an adaptive PVARP in either a rate-adaptive or non-rate-adaptive pacemaker. The algorithm begins at block 60 with the initialization or programming of values for MTR, Prog-PVARP and certain constants M, N, P and R.

As will become apparent as the description of the invention continues, N is a multiplier for a quantity of time to be added to PVARP and is incremented for each PMT episode (e.g., unity) and decremented (e.g., 0.5) every M days, but is always positive. M, then, is the number of time units, typically measured in days or months, but also possibly measured by 5–100 beats and then switching to days or months or years between decrements of N. P is a number of beats at MTR (e.g., 16 beats) and is used to differentiate pacemaker Wenckebaching from a PMT. PROG.-PVARP is an initial program value of PVARP selected by the cardiologist. R is a time increment to be added to PVARP (e.g., 20 ms). Following the initialization steps, PVARP is set equal to the program value of PVARP plus the factor N*R at block 62. A test is then made at block 64 to determine whether M time units have gone by since a preceding decrement of M and, if not, control exits to decision block 66. By measuring the V—V interval between successive ventricular stimulating pulses, the ventricular pacing rate can be determined. The test at block 66 determines whether the ventricular pacing rate has risen to MTR and, if not, control returns, via path 68, whereby step 62 is again repeated.

When the test at decision block 66 reveals that the pacing rate has become equal to MTR, a further test is made at block 70 to determine whether a predetermined number of successive ventricular beats, P, have taken place where the ventricular pacing rate has remained at MTR. Typically, the value, P, may be an arbitrary number, such as 16 beats. If the predetermined number of beats at MTR has not occurred, control again returns, via path 72, to the input of block 62.

When it is determined that the pacemaker is pacing the ventricle at MTR for the predetermined number of beats, it is indicative that a PMT is in progress and the algorithm provides for increasing PVARP to a value typically in the range of from 350 to 500 milliseconds, such as, for example, 400 milliseconds for one beat. This is indicated in the block diagram of FIG. 3 by block 74. By increasing PVARP to, say, 400 milliseconds, it is highly likely that the PMT will be broken, since PVARP approaches the AA interval, and any retrograde conducted ventricular stimulating pulses would have taken place during the extended PVARP.

Following the breaking of the detected PMT, the value of N is incremented and the value of M is reset to zero. See block 76. Control then returns, via path 78, to the input of operation block 62. With N incremented by 1, the new value of PVARP will be the previously programmed PVARP value plus the product of the incremented value of N and the time value, R.

The foregoing sequence of operations and tests is carried out with the value of PVARP increasing by successively increasing time increments each time a PMT episode is detected. If the test at decision block 64 reveals that M time units have elapsed since a preceding episode of PMT, a test is made at decision block 80 to determine whether N is still greater than 0. If it is, it is decremented as represented by block 82 with the value of M being reset to 0. If either the test made at decision block 80 reveals that N equals 0 or if the operation performed at block 82 is completed, control returns, via path 84, 86, 88 and 90, to again determine whether the ventricular pacing rate has become equal to the maximum tracking rate reflected by decision block 66 in the flow diagram of FIG. 3.

Figure 4:
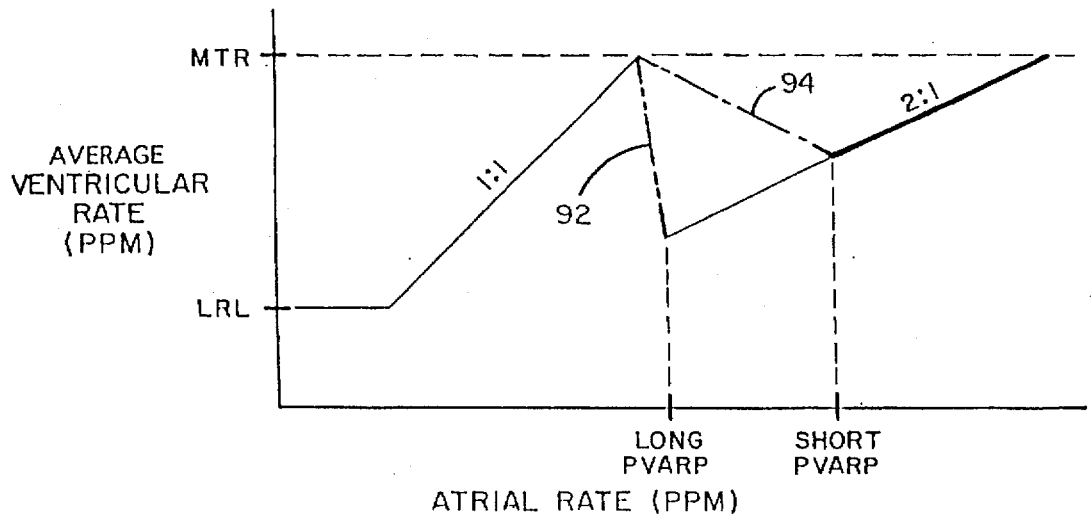
FIG. 4 is a DDD pacing transfer function illustrating the effects of small and large PVARP values.

Referring to FIG. 4, there is illustrated a plot of a transfer function for a dual chamber pacer that helps illustrate the effects of small and large PVARP values on the ventricular pacing rate. Here, the average ventricular rate in pulses per minute is plotted as a function of atrial rate. As the atrial rate increases, the ventricular rate tracks one for one until the maximum tracking rate is reached. With a long PVARP, electronic Wenckebaching causes a steep drop in the ventricular rate, as represented by the dashed line 92 in FIG. 4. However, with a small PVARP, the ventricular rate drops less precipitously to a 2:1 tracking mode as indicated by the dot-dash line 94.

The algorithm represented by FIG. 3 insures that PVARP will adapt to a value that is a minimum, while insuring that PMTs are appropriately addressed. As shown in FIG. 4, by keeping PVARP as short as possible, the drop in the ventricular pacing rate due to pacemaker Wenckebaching is not as drastic as would be the case where PVARP is large.

By way of summary, there has been shown and described a dual chamber, rate-responsive or non-rate-responsive cardiac pacemaker so as to minimize the occurrence of pacemaker induced tachycardia by providing for an adaptive PVARP. The device is capable of sensing when the ventricular pacing rate becomes equal to the maximum atrial tracking rate over a predetermined number of beats as an indicator of an episode of PMT, and then responds by incrementing PVARP by a time interval sufficiently long so that retrograde conducted P-waves will tend not to fall outside of the incremented PVARP time interval. This increased PVARP time interval persists only for a single beat and is therefore sufficient in most cases to terminate the PMT. To decrease the likelihood that a subsequent PMT episode will occur, the base value of PVARP is increased by a predetermined time increment each time a PMT is sensed. Where no PMTs occur over a prolonged predetermined period, measured in days, months, or even a year, the algorithm decrements the then existing PVARP value to thereby prevent false positive PMT detections from causing the PVARP to rachet upward, or to allow PVARP to automatically return to a short value once the cause of the PMT has passed. It can be seen then that the algorithm provides an adaptive PVARP that tends to be as small as possible without recurrent episodes of PMT.

The dual chamber cardiac pacemaker of the prevent invention, when programmed to include both dynamic AV interval and automatic PVARP in accordance herewith, can provide a dynamic TARP that is sufficiently short that the electronic Wenckebach rate drop illustrated in FIG. 4 is virtually eliminated.

What is claimed is:

1. A dual chamber cardiac pacemaker comprising:
   (a) means for sensing atrial depolarization events;
   (b) means for sensing ventricular depolarization events;
   (c) means for stimulating a ventricular chamber;
   (d) first timing means coupled to the means for sensing atrial depolarization events for establishing an AV interval between the occurrence of an atrial depolarization event and the time following such occurrence at which the ventricular chamber stimulating means stimulates the ventricular chamber;
   (e) second timing means coupled to the means for sensing ventricular depolarization events for establishing a PVARP time interval during which the first timing means is inhibited from initiating an AV interval;
   (f) means for detecting the occurrence of pacemaker mediated tachycardia episodes; and
   (g) means responsive to the detecting means and coupled to the second timing means for increasing the PVARP time interval for at least one beat by a time value in the range of from 350 milliseconds to 500 milliseconds that is sufficient to insure that retrograde P-waves are not tracked by the means for stimulating a ventricular chamber.

2. The dual chamber cardiac pacemaker as in claim 1 wherein the means for detecting the occurrence of pacemaker mediated tachycardia episodes comprises means, including the atrial sensing means, for detecting retrograde P-waves occurring subsequent to the expiration of the PVARP time interval.

3. The dual chamber cardiac pacemaker as in claim 1 and further including means for periodically subtracting a time interval decrement value from an extended PVARP time interval when the detecting means fails to detect an episode of PMT during a predetermined time period.

4. The dual chamber cardiac pacemaker as in claim 3 wherein the predetermined time period is in the range of from less than one day to at least six months.

5. The dual chamber cardiac pacemaker as in claim 1 wherein the value to which the PVARP time interval is extended for one beat is 400 milliseconds.

6. The dual chamber cardiac pacemaker as in claim 1 wherein the first predetermined time increment value is in the range of from one millisecond to 100 milliseconds.

7. The dual chamber cardiac pacemaker as in claim 3 wherein the decrement value is in the range of from 5 to 15 milliseconds.

8. The dual chamber cardiac pacemaker as in claim 7 wherein the predetermined time interval decrement value is 10 milliseconds and the predetermined time period is in the range of from one second or one cardiac cycle to one month.

9. A method of operating a dual chamber cardiac pacemaker to avoid pacemaker-induced tachycardia, the pacemaker being of the type which senses atrial depolarization events and ventricular depolarization events, applies a stimulating pulse to ventricular tissue, and establishes an AV delay interval, a base PVARP time interval and a maximum tracking rate for tracking sensed atrial depolarization events, comprising the steps of:
   (a) sensing when stimulation of ventricular tissue is occurring at the maximum atrial tracking rate over a predetermined number of beats;
   (b) increasing the PVARP time interval for at least one beat from the base PVARP value to a value insuring that retrograde conducted P-waves will not fall outside of the increased PVARP time interval and thereafter
   (c) extending the base PVARP value by a predetermined PVARP increment value, each time the condition of step (a) is detected.

10. The method as in claim 9 and further including the step of periodically decreasing the extended PVARP base value toward the PVARP base value when the condition of step (a) is not sensed during a predetermined time period.

11. A dual chamber cardiac pacemaker having means for establishing an AV delay interval that varies with a pacing rate parameter of the pacemaker and means for determining a PVARP value sufficient to preclude PMT, the sum of said AV interval and said PVARP value being sufficiently short to minimize a drop in pacing rate due to electronic Wenckebaching.

\* \* \* \* \*